(12) United States Patent
Berthon-Jones

(10) Patent No.: US 7,661,428 B2
(45) Date of Patent: *Feb. 16, 2010

(54) DETERMINATION OF LEAK AND RESPIRATORY AIRFLOW

(75) Inventor: Michael Berthon-Jones, Leonay (AU)

(73) Assignee: Resmed Limited, New South Wales (AU)

( * ) Notice: Subject to any disclaimer, the term of this patent is extended or adjusted under 35 U.S.C. 154(b) by 819 days.

This patent is subject to a terminal disclaimer.

(21) Appl. No.: 11/223,237

(22) Filed: Sep. 8, 2005

(65) Prior Publication Data

US 2006/0005835 A1 Jan. 12, 2006

Related U.S. Application Data

(63) Continuation of application No. 10/726,114, filed on Dec. 1, 2003, now Pat. No. 6,945,248, which is a continuation of application No. 09/902,011, filed on Jul. 10, 2001, now Pat. No. 6,659,101, which is a continuation of application No. 09/525,042, filed on Mar. 14, 2000, now Pat. No. 6,279,569, which is a continuation of application No. 08/911,513, filed on Aug. 14, 1997, now Pat. No. 6,152,129.

(30) Foreign Application Priority Data

Aug. 14, 1996 (AU) ..................... PO1638

(51) Int. Cl.
A61M 16/00 (2006.01)

(52) U.S. Cl. ............... 128/204.22; 128/204.18; 128/204.21; 128/204.23; 128/204.26; 128/200.24; 600/484; 600/529; 600/533; 600/538

(58) Field of Classification Search ............ 128/200.24, 128/202.22, 204.18, 204.21, 204.26, 207.14, 128/207.18; 600/484, 529, 533, 538
See application file for complete search history.

(56) References Cited

U.S. PATENT DOCUMENTS 3,903,881 A * 9/1975 Weigl ..................... 128/204.25
4,587,967 A 5/1986 Chu et al.

(Continued)

FOREIGN PATENT DOCUMENTS

AU A 39130 11/1995

(Continued)

OTHER PUBLICATIONS

Cohen et al. "Breath Detection using Fuzzy Sets and Sensor Fusion", Proceedings of the Annual International Conference of the IEEE Engineering in Medicine and Biology Society, New York, IEEE, vol. 16, 1994 pp. 1067-1068; ISBN: 0-7803-2051-4.

(Continued)

Primary Examiner—Justine R Yu
Assistant Examiner—Clinton Ostrup
(74) Attorney, Agent, or Firm—Gottlieb Rackman & Reisman P.C.

(57) ABSTRACT

Methods and apparatus for determining leak and respiratory airflow are disclosed. A pressure sensor (34) and a differential pressure sensor (32) have connection with a pneumotach (24) to derive instantaneous mask pressure and airflow respectively. A microcontroller (38) estimates a non-linear conductance of any leak path occurring at a mask (12) as being the low pass filtered instantaneous airflow divided by the low pass filtered square root of the instantaneous pressure. The instantaneous leak flow is then the conductance multiplied by the square root of the instantaneous pressure, and the respiratory airflow is calculated as being the instantaneous airflow minus the instantaneous leak flow. The time constants for the low pass filtering performed by the microcontroller (38) can be dynamically adjusted dependent upon sudden changes in the instantaneous leak flow.

6 Claims, 10 Drawing Sheets

U.S. PATENT DOCUMENTS

| | | | |
|---|---|---|---|
| 4,674,492 A | 6/1987 | Niemeyer | |
| 5,107,830 A | 4/1992 | Younes | |
| 5,303,700 A | 4/1994 | Weismann et al. | |
| 5,433,193 A | 7/1995 | Sanders et al. | |
| 5,535,738 A | 7/1996 | Estes et al. | |
| 5,551,419 A | 9/1996 | Froehlich et al. | |
| 5,598,838 A | 2/1997 | Servidio et al. | |
| 5,632,269 A | 5/1997 | Zdrojkowski | |
| 5,794,615 A | 8/1998 | Estes | |
| 5,799,652 A | 9/1998 | Kotliar | |
| 5,803,065 A | 9/1998 | Zdrojkiwski et al. | |
| 5,865,174 A | 2/1999 | Kloppel | |
| 5,970,975 A | 10/1999 | Estes et al. | |
| 6,006,748 A | 12/1999 | Hollis | |
| 6,029,660 A | 2/2000 | Calluaud et al. | |
| 6,119,686 A | 9/2000 | Somerson et al. | |
| 6,142,150 A | 11/2000 | O'Mahoney | |
| 6,152,129 A | 11/2000 | Berthon-Jones | |
| 6,279,569 B1 | 8/2001 | Berthon-Jones | |
| 6,345,619 B1 | 2/2002 | Finn | |
| 6,349,724 B1 | 2/2002 | Burton et al. | |
| 6,425,395 B1 | 7/2002 | Brewer et al. | |
| 6,532,957 B2 | 3/2003 | Berthon-Jones | |
| 6,945,248 B2 * | 9/2005 | Berthon-Jones | 128/204.21 |

FOREIGN PATENT DOCUMENTS

| | | |
|---|---|---|
| EP | 0606687 | 12/1993 |
| EP | A 0714670 | 4/1995 |
| GB | 2077444 | 6/1981 |
| WO | WO 9211054 | 6/1991 |

OTHER PUBLICATIONS

Klir et al., "Fuzzy Sets and Fuzzy Logic: Theory and Applications", Prentice Hall Inc., Saddle River, New Jersey, 1995, ISBN 0-13-101171-5; p. 50-51, 327-338.

* cited by examiner

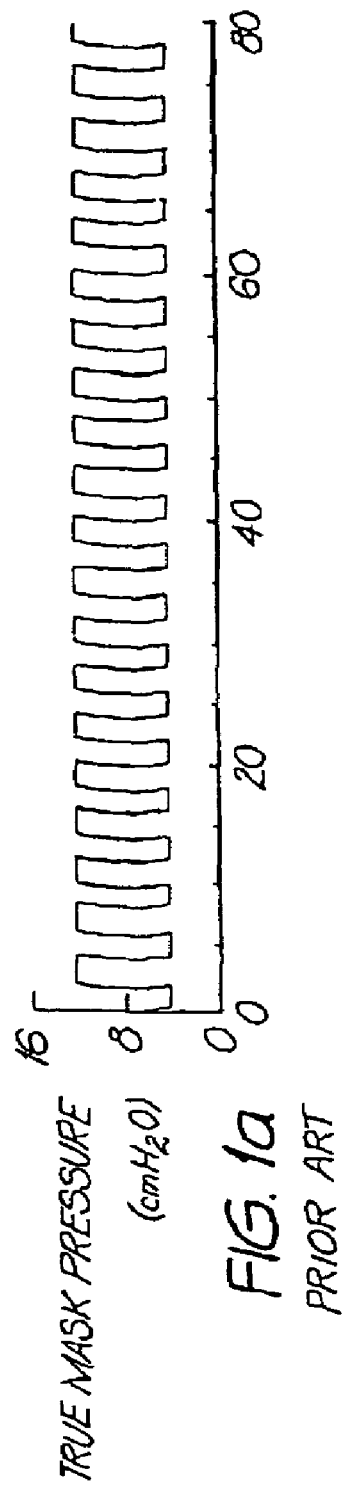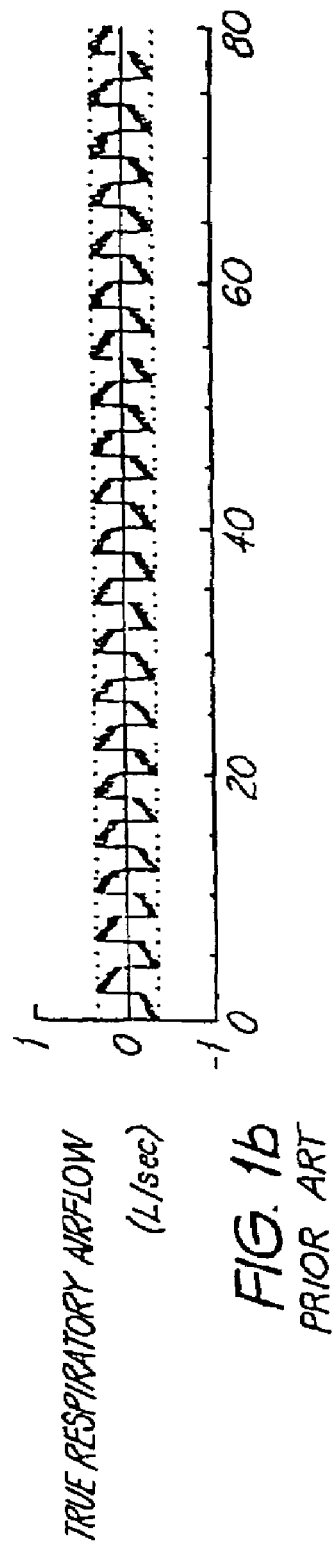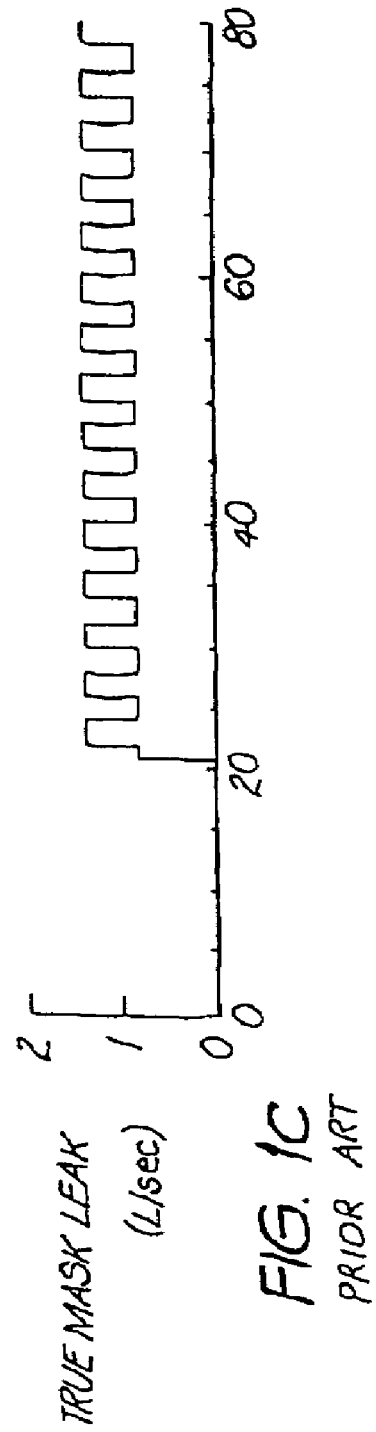

MEASURED MASK FLOW (L/sec)

CALCULATED LEAK (L/sec)

CALCULATED RESP. AIRFLOW (L/sec)

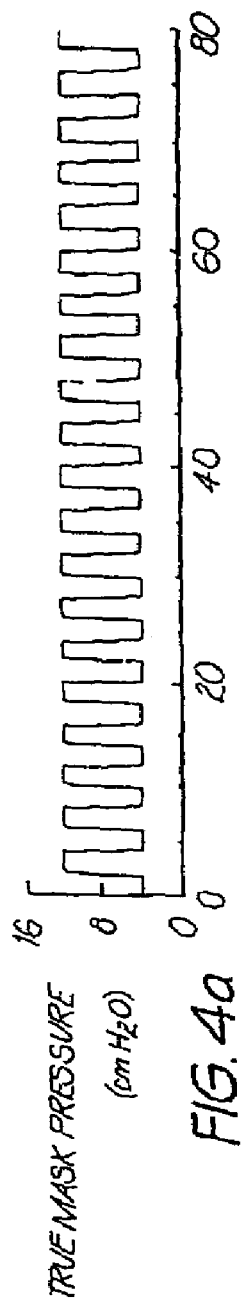
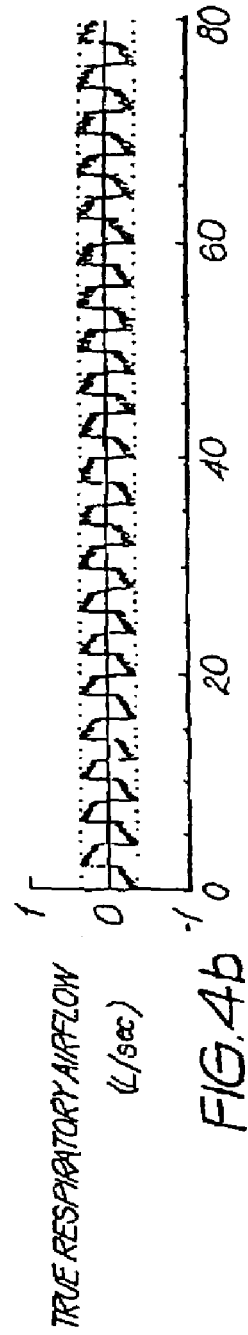
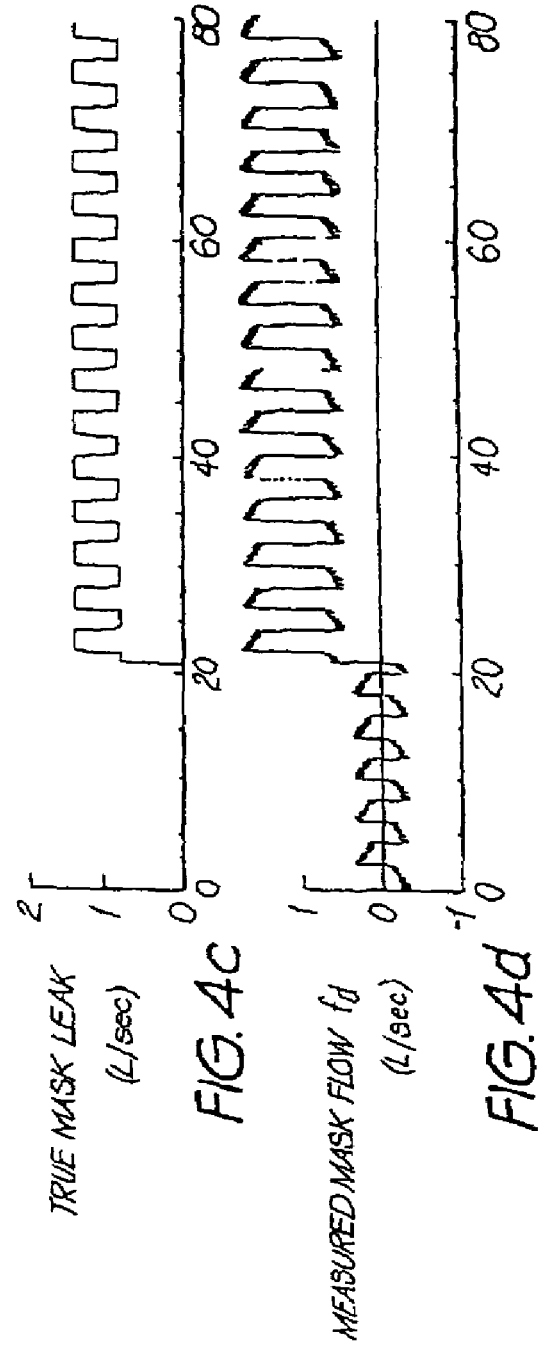
FIG. 4a TRUE MASK PRESSURE (cm H₂O)
FIG. 4b TRUE RESPIRATORY AIRFLOW (L/sec)
FIG. 4c TRUE MASK LEAK (L/sec)
FIG. 4d MEASURED MASK FLOW fd (L/sec)

US 7,661,428 B2

DETERMINATION OF LEAK AND RESPIRATORY AIRFLOW

This application is a continuation of application Ser. No. 10/726,114 filed on Dec. 1, 2003 now U.S. Pat. No. 6,945, 248, now allowed, which is a continuation of application Ser. No. 09/902,011 filed on Jul. 10, 2001, now U.S. Pat. No. 6,659,101, which is a continuation of application Ser. No. 09/525,042 filed on Mar. 14, 2000, now U.S. Pat. No. 6,279, 569, which is a continuation of application Ser. No. 08/911, 513 filed on Aug. 14, 1997, now U.S. Pat. No. 6,152,129.

FIELD OF THE INVENTION

The invention relates to methods and apparatus for the determination of leakage airflow and true respiratory airflow, particularly during mechanical ventilation.

The airflow determination can be for a subject who is either spontaneously or non-spontaneously breathing, or moves between these breathing states. The invention is especially suitable for, but not limited to, normally conscious and spontaneously breathing human subjects requiring long term ventilatory assistance, particularly during sleep.

BACKGROUND OF THE INVENTION

In this specification any reference to a "mask" is to be understood as including all forms of devices for passing breathable gas to a person's airway, including nose masks, nose and mouth masks, nasal prongs/pillows and endotracheal or tracheostomy tubes.

During mechanical ventilation, breathable gas is supplied for example via a mask, at a pressure which is higher during inspiration and lower during expiration. It is useful to measure the subject's respiratory airflow during mechanical ventilation to assess adequacy of treatment, or to control the operation of the ventilator.

Respiratory airflow is commonly measured with a pneumotachograph placed in the gas delivery path between the mask and the ventilator. Leaks between the mask and the subject are unavoidable. The pneumotachograph measures the sum of the respiratory airflow plus the flow through the leak. If the instantaneous flow through the leak is known, the respiratory airflow can be calculated by subtracting the flow through the leak from the flow at the pneumotach.

Known methods to correct for the flow through the leak assume (i) that the leak is substantially constant, and (ii) that over a sufficiently long time, inspiratory and expiratory respiratory airflow will cancel. If these assumnptions are met, the average flow through the pneumotach over a sufficiently long period will equal the magnitude of the leak, and the true respiratory airflow may then be calculated as described.

The known method is only correct if the pressure at the mask is constant. If the mask pressure varies with time (for example, in the case of a ventilator), assumption (i) above will be invalid, and the calculated respiratory airflow will therefore be incorrect. This is shown markedly in FIGS. 1a-1f.

FIG. 1a shows a trace of measured mask pressure in bi-level CPAP treatment between about 4 cm $H_2O$ on expiration and 12 cm $H_2O$ on inspiration. FIG. 1b shows a trace of true respiratory airflow in synchronism with the mask pressures. At time=21 seconds a mask leak occurs, resulting in a leakage flow from the leak that is a function of the treatment pressure, as shown in FIG. 1c. The measured mask flow shown in FIG. 1d now includes an offset due to the leak flow. The prior art method then determines the calculated leak flow over a number of breaths, as shown in FIG. 1e. The resulting calculated respiratory flow, as the measured flow minus the calculating leak flow is shown in FIG. 1f, having returned to the correct mean value, however is incorrectly scaled in magnitude, giving a false indication of peak positive and negative airflow.

Another prior art arrangement is disclosed in European Publication No. 0 714 670 A2, including a calculation of a pressure-dependent leak component. The methodology relies on knowing precisely the occurrence of the start of an inspiratory event and the start of the next inspiratory event. In other words, the leak calculation is formed as an average over a known breath and applied to a subsequent breath.

This method cannot be used if the moment of start and end of the previous breath are unknown. In general, it can be difficult to accurately calculate the time of start of a breath. This is particularly the case immediately following a sudden change in the leak.

Furthermore, the method will not work in the case of a subject who is making no respiratory efforts, and is momentarily not being ventilated at all, for example during an apnea, because for the duration of the apnea there is no start or end of breath over which to make a calculation.

The present invention seeks to provide a determination of leak flow and true respiratory airflow, accounting for the variations in flow through a leak as a function of pressure.

SUMMARY OF THE INVENTION

The invention discloses a method for determining instantaneous leak flow at a mask having a leak path during mechanical ventilation, the method comprising the steps of:

(a) determining instantaneous airflow at the mask;

(b) determining instantaneous pressure at the mask;

(c) estimating non-linear conductance of said leak path as the low-pass filtered instantaneous airflow divided by the low-pass filtered square root of the instantaneous pressure; and (d) determining said instantaneous leak flow to be said conductance multiplied by the square root of the said instantaneous pressure.

The invention further discloses a method for determining instantaneous respiratory airflow for a subject receiving breathable gas by a mask and in the presence of any mask leak, the method comprising the steps of:

(a) determining instantaneous airflow at the mask;

(b) determining instantaneous pressure at the mask;

(c) estimating non-linear conductance of said leak path as the low pass filtered instantaneous airflow divided by the low pass filtered square root of the instantaneous pressure;

(d) determining instantaneous leak flow to be said conductance multiplied by the square root of the said instantaneous pressure; and (e) calculating the respiratory airflow as the instantaneous airflow minus the instantaneous leak flow.

The invention yet further discloses apparatus for determining respiratory airflow for a subject receiving breathable gas by a mask and in the presence of any mask leak, the apparatus comprising:

transducer means located at or proximate the mask to determine instantaneous mask airflow and pressure; and processing means for estimating non-linear conductance of said leak path as the low pass filtered instantaneous airflow divided by the low pass filtered square root of the instantaneous pressure, determining instantaneous leak flow to be said conductance multiplied by the square root of the said instantaneous pressure, and calculating the respiratory airflow as the instantaneous airflow minus the instantaneous leak flow.

The invention yet further discloses apparatus for providing continuous positive airway pressure treatment or mechanical ventilation, the apparatus comprising:

a turbine for the generation of a supply of breathable gas;

a gas delivery tube having connection with the turbine;

a mask having connection to the delivery tube to supply said breathable gas to a subject's airway;

transducer means located at or proximate the mask to determine instantaneous mask airflow and pressure;

processor means for estimating non-linear conductance of said leak path as the low pass filtered instantaneous airflow divided by the low pass filtered square root of the instantaneous pressure, determining instantaneous leak flow to be said conductance multiplied by the square root of the said instantaneous pressure, and calculating the respiratory airflow as the instantaneous airflow minus the instantaneous leak flow; and control means to control the flow generator to, in turn, control the mask pressure and/or mask airflow on the basis of the calculated respiratory airflow.

The invention yet further discloses a computer program for executing the steps referred to above.

In one preferred form, time constants of the low pass filtering are dynamically adjusted dependent upon sudden changes in the instantaneous leak flow.

Embodiments of the invention provide advantages over the prior art. There is no need to know when transitions between respiratory phases occurs. The independence from knowledge of the subject's respiratory state has the important result that the leak flow calculation is accurate in apneic (i.e. no flow) instances on the part of the subject or the mechanical ventilator.

BRIEF DESCRIPTION OF THE DRAWINGS

Embodiments of the invention will now be described with reference to the accompanying drawings in which:

FIGS. 1a-1f shows traces of pressure and airflow from which respiratory airflow is calculated in accordance with a prior art method;

DETAILED DESCRIPTION OF PREFERRED EMBODIMENTS

Figure 2A:
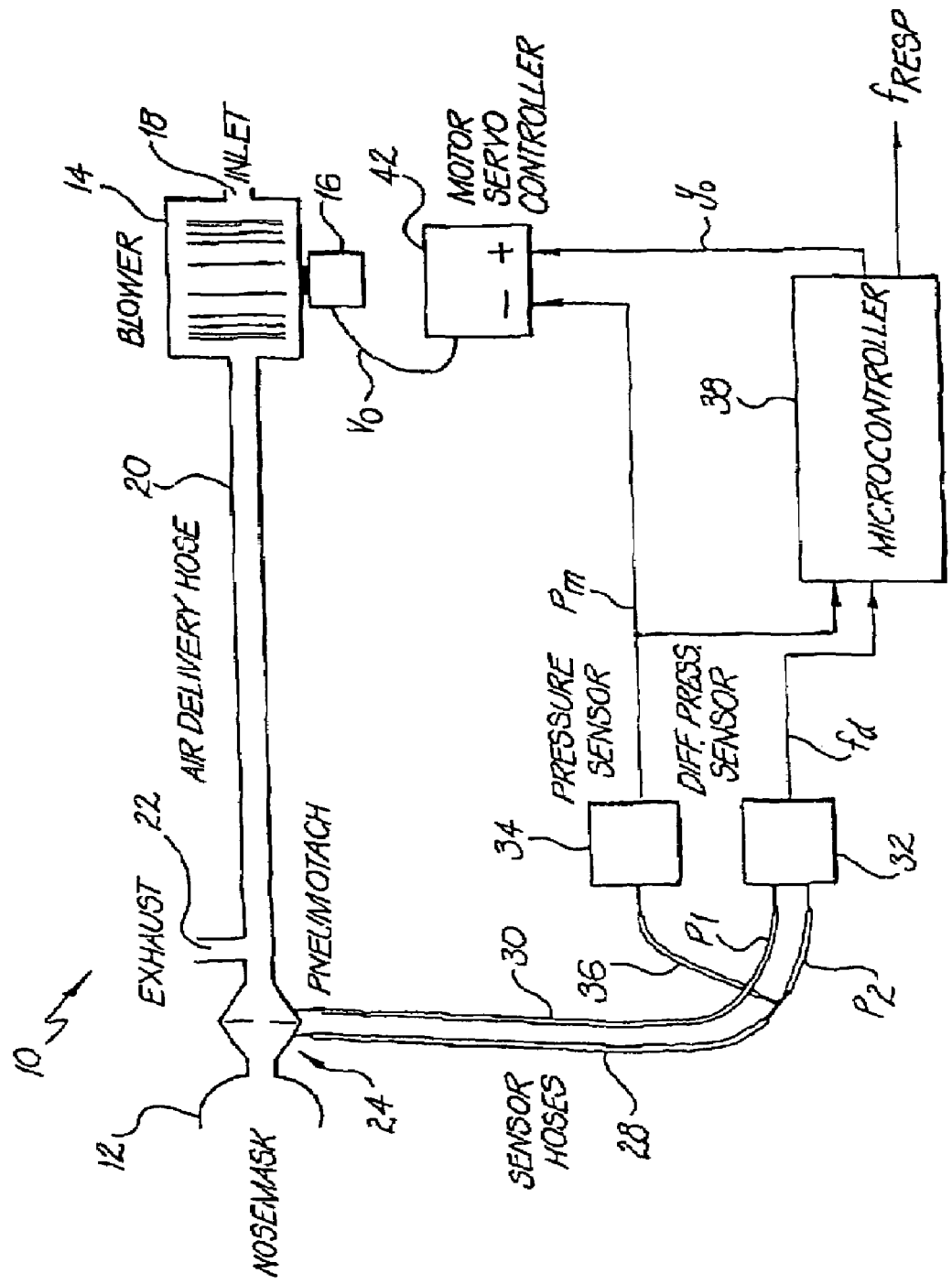
FIGS. 2a and b show schematic diagrams of two embodiments of ventilatory assistance apparatus.

FIG. 2a shows mechanical ventilation apparatus 10 embodying the invention.

The subject/patient wears a nose mask 12 of any known type. The subject equally could wear a face mask or nasal prongs/pillows, or alternatively have an endotracheal tube or tracheostomy tube in place. A turbine/blower 14, operated by a mechanically coupled electrical motor 16, receives air or breathable gas at an inlet 18 thereof, and supplies the breathable gas at a delivery pressure to a delivery tube/hose 20 having connection at the other end thereof with the nose mask 12. Breathable gas thus is provided to the subject's airway for the purpose of providing assisted respiration, with the subject's expired breath passing to atmosphere by an exhaust 22 in the delivery tube 20, typically located proximate to the mask 12.

A pneumotachograph 24 is placed in the delivery tube 20 between the mask 12 and the exhaust 22 to provide two pressure signals, $P_2$ and $P_1$, across the pneumotachograph, each passed by hoses 28,30 to a differential pressure sensor 32. A determination of the flow of gas in the mask 12 is made the differential pressure, $P_2-P_1$, resulting in a flow signal $f_d$. The mask pressure, $P_2$, also is passed to a pressure sensor 34 by a tapped line 36 taken from the respective hose 28, to generate a delivery pressure signal, $p_m$, output from the pressure sensor 34.

Both the flow signal, $f_d$, and the pressure signal, $p_m$, are passed to a microcontroller 38 where they are sampled for subsequent signal processing, typically at a rate of 50 Hz.

The microcontroller 38 is programmed to process the flow and pressure signals ($f_d$, $P_m$) to produce an output control signal, $y_o$, provided to an electronic motor servo-controller 42 that, in turn, produces a motor speed control output signal, $v_o$. This signal is provided to the motor 16 to control the rotational speed of the turbine 14 and provide the desired treatment pressure, $P_2$, at the nose mask 12.

The motor servo-controller 42 employs a negative feedback control technique that compares the actual delivery pressure, in the form of the signal $p_m$, with the control signal $y_o$. For convenience, this control stratagem may be independent of operation of the microcontroller 38.

Operation of the controlling microcontroller 38, so far as a calculation of respiratory airflow is concerned, broadly is as follows. In a sampled manner, the conductance of any mask leak is calculated, then the instantaneous flow through the leak is calculated. The flow through the leak is subtracted from the total mask flow to calculate the true instantaneous respiratory airflow.

Figure 1D:
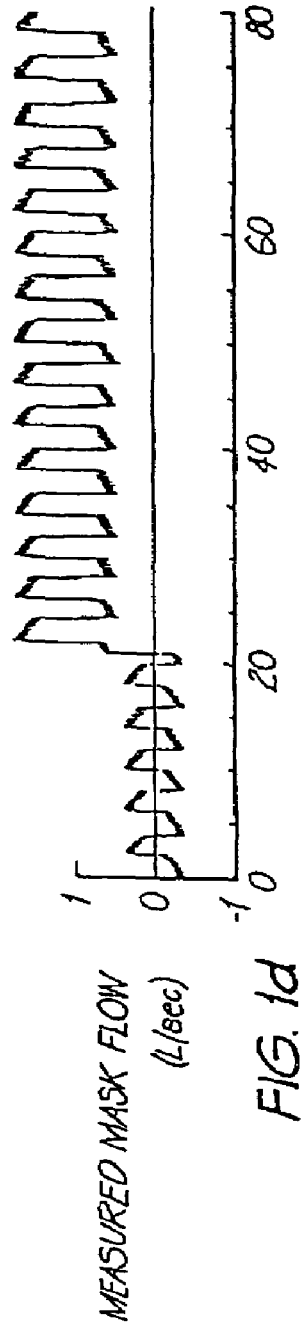
Figure 1E:
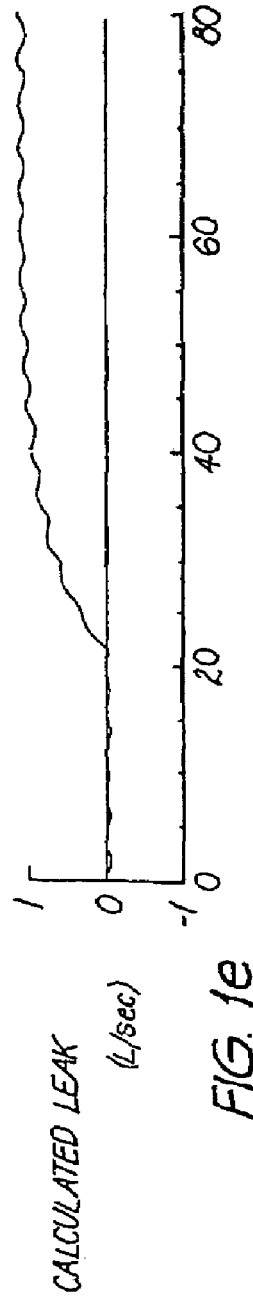
Figure 1F:
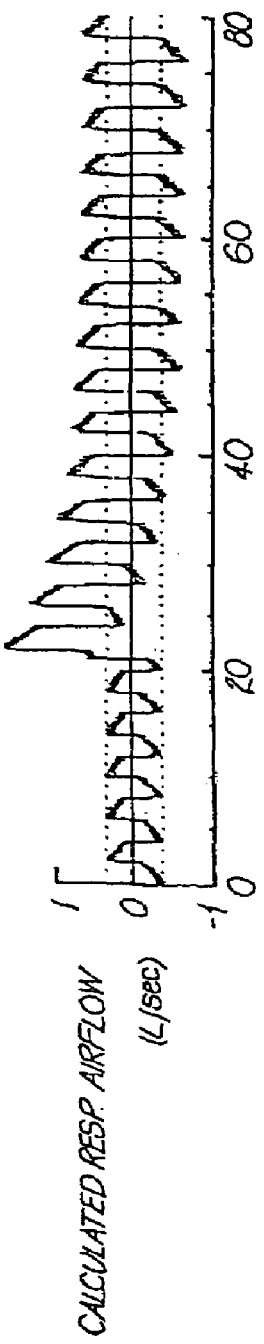
Figure 2B:
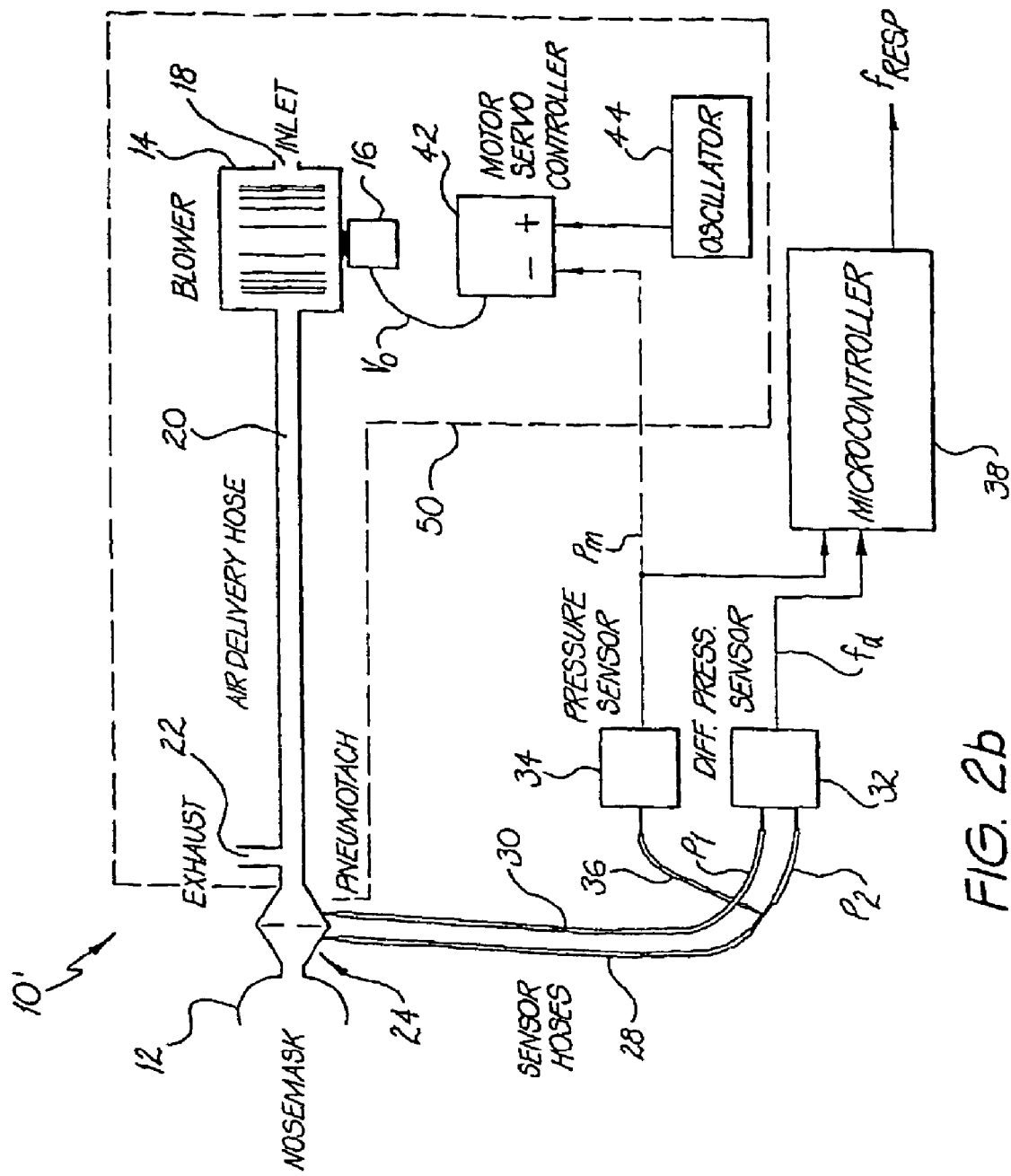

FIG. 2b shows an alternative embodiment of a system for determining true respiratory airflow during mechanical ventilation. The mechanical ventilation system 10' of FIG. 1b differs from that of FIG. 1a firstly in that the microcontroller 38 plays no part in control of the ventilator 50, rather only receives and data processes the electrically transduced mask pressure and flow signals $p_m$, $f_d$ to determine and generate the instantaneous respiratory flow $f_{RESP}$. The ventilator 50 has an internal drive signal provided by an oscillator 44. The motor servo controller also may or may not receive the mask pressure signal $p_m$ as a form of feedback control. Indeed, the ventilator 50 can be realised by any convenient form of known generic ventilation device.

Figure 3:
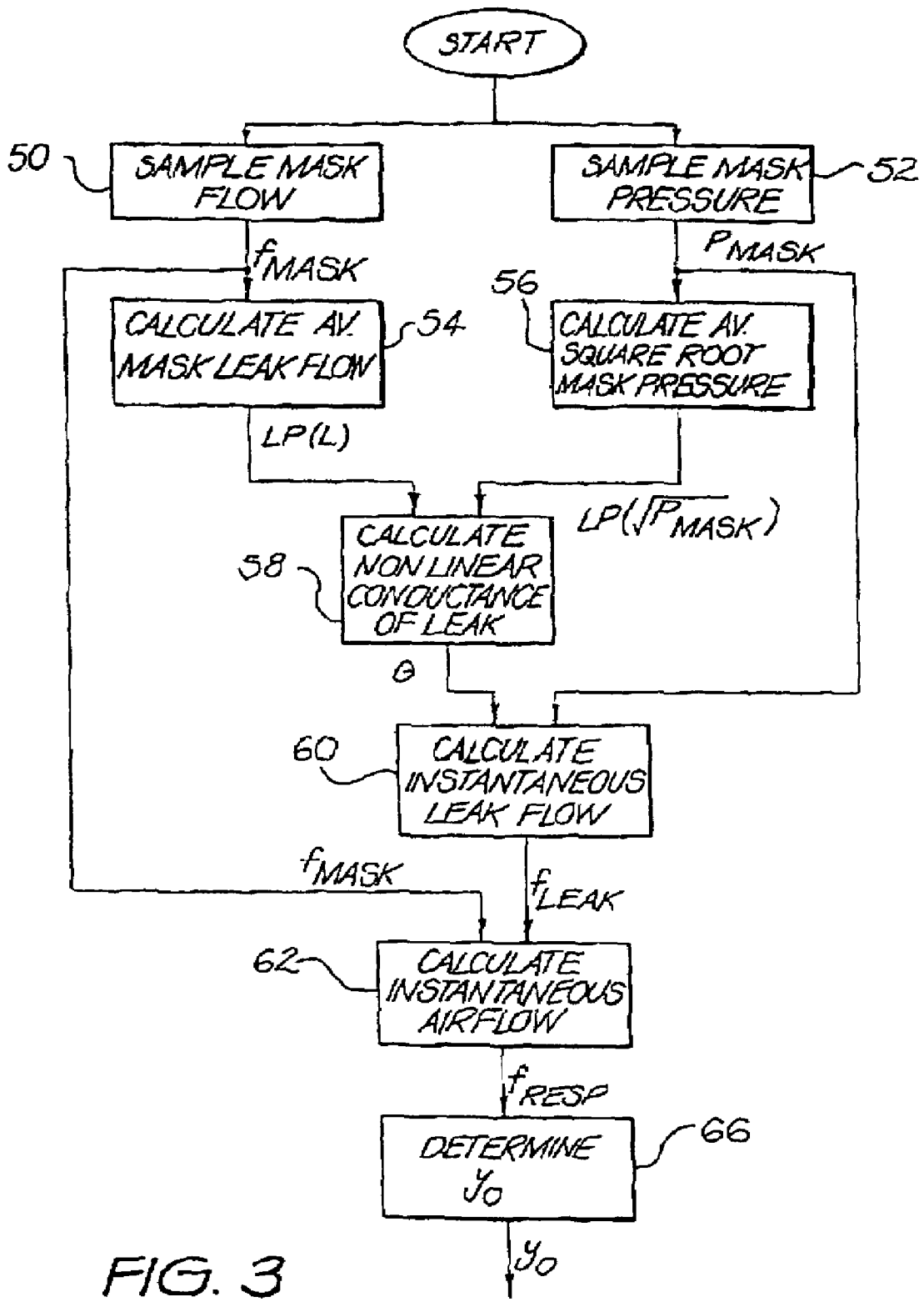
FIG. 3 is a block flow diagram of a method for determining instantaneous respiratory airflow.

The controlling software resident within the microcontroller 38 performs the following steps in determining the respiratory airflow as broadly described above, as also shown in the flow diagram of FIG. 3.

The word "average" is used herein in the most general sense of the result of a low pass filtering step, and is not confined to an arithmetic mean.

1. Repeatedly sample the mask airflow $f_d$ to give a sampled signal $f_{MASK}$, and the mask pressure $P_m$ to give a sampled signal $P_{MASK}$, for example at intervals of T=20 milliseconds. (Steps 50,52).
2. Calculate the average leak, LP(L), as being the result of low pass filtering the airflow, $f_{MASK}$, with a time constant of 10 seconds. (Step 54).
3. Calculate the average of the square root of the mask pressure, $LP(\sqrt{P_{MASK}})$, as being the result of low pass filtering the square root of the mask pressure, $P_{MASK}$, with a time constant of 10 seconds. (Step 56).
4. Calculate the conductance, G, of any leak (Step 58), from the equation:

$G = LP(L)/LP(\sqrt{P_{MASK}})$

5. Calculate the instantaneous leak flow, $f_{LEAK}$, through the leak (Step 60), from the equation:

$f_{LEAK} = G\sqrt{P_{MASK}}$

If there is no leak flow, the value of LP(L) will be equal to zero, as will G and hence $f_{LEAK}$. Thus the methodology is valid also where leak is equal to zero—no leak.
   At this juncture the leak flow has been determined, such as would be desired for a leak flow detector. If desired, the instantaneous respiratory airflow can be subsequently determined by the following step.
6. Calculate the instantaneous respiratory airflow, $f_{RESP}$, by subtracting the instantaneous leak from the mask flow (Step 62):

$f_{RESP} = f_{MASK} - f_{LEAK}$

Figure 4E:
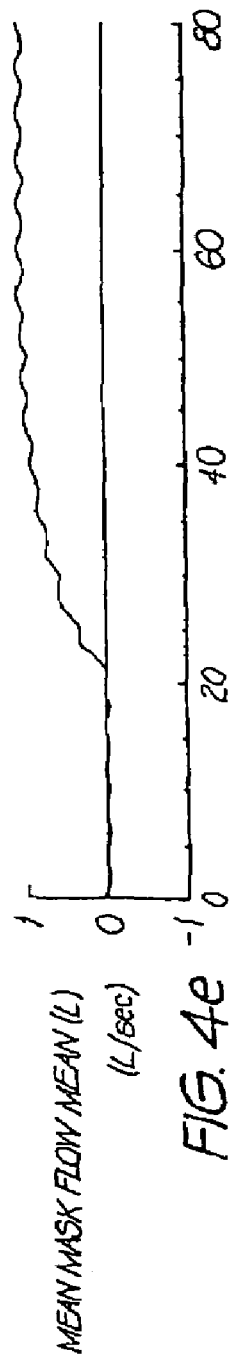
FIG. 4 shows traces of pressure, airflow and other variables from which respiratory airflow is calculated.
Figure 4F:
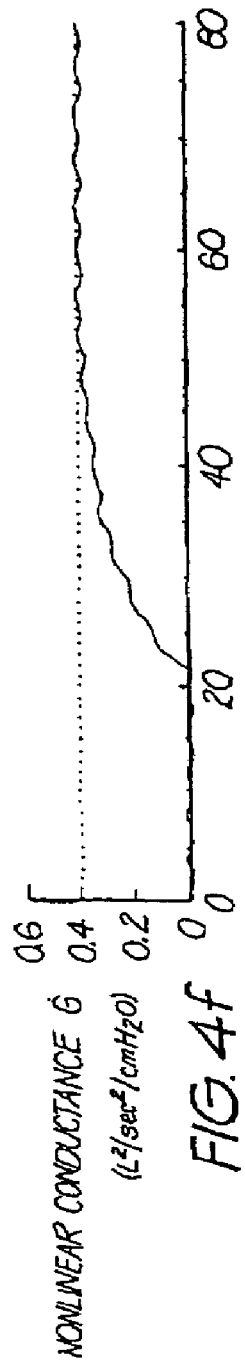
Figure 4G:
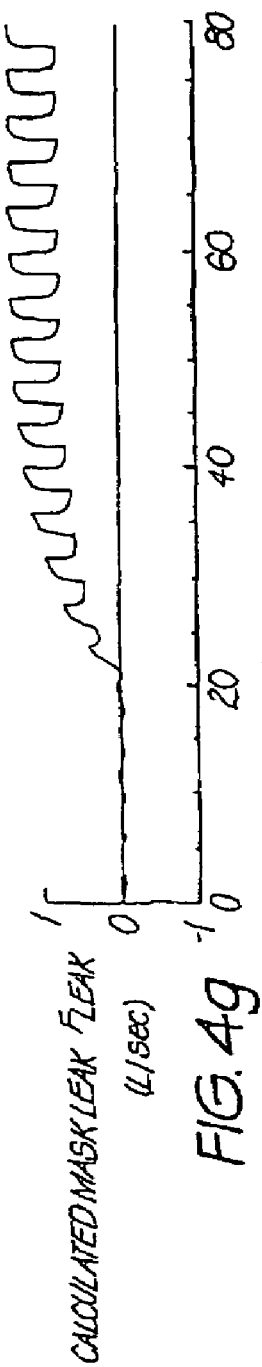
Figure 4H:
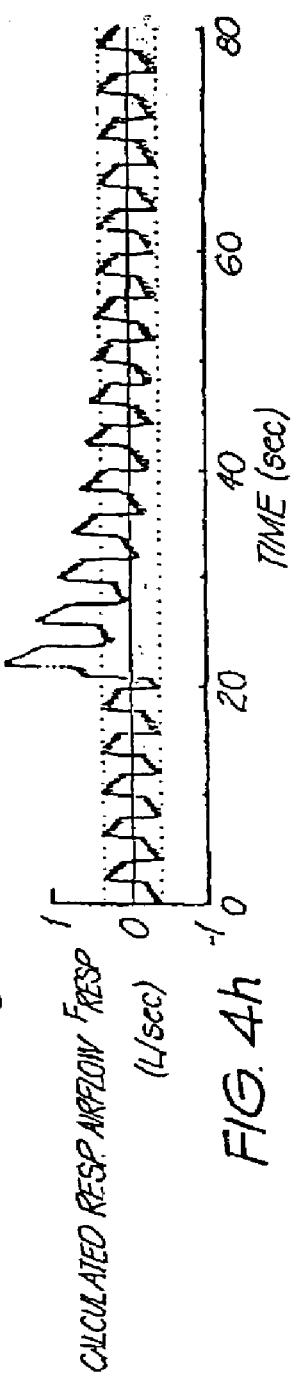

FIGS. 4a-4h illustrate the methodology of the embodiment described above with reference to FIG. 2b. At time, t=21 sec, a continuing leak of approximately 1 l/sec is introduced. FIG. 4e shows the mean mask flow. FIG. 4f represents the calculated conductance G, from which the mask leak flow can be estimated as shown in FIG. 4g. Finally, FIG. 4h shows how the calculated respiratory airflow recovers within approximately 30 seconds, and, importantly, gives the correctly scaled (true) magnitude of airflow.

With regard to setting the instantaneous output signal $y_o$, the microcontroller broadly executes the following steps:

7. If the calculated true respiratory airflow $f_{RESP}$ is above a threshold, for example 0.05 L/sec. $y_o$ is set to a value corresponding to an inspiratory pressure, $P_{INSP}$. Otherwise $y_o$ is set to a value corresponding to an expiratory pressure, $P_{EXP}$. In general, $P_{INSP}$ is higher than $P_{EXP}$, but in the case of continuous positive airways pressure, $P_{EXP}$ may be equal to $P_{INSP}$. (Step 66).

It is to be understood that many other methods of determining $y_o$ from $f_{MASK}$ may be used in step 7, for example as described in the text *Principles and Practice of Mechanical Ventilation*, edited by Martin J. Tobin (McGraw Hill Inc, 1994).

In order to control ventilation, it is necessary to measure the subject's ventilation. In the presence of a leak, the ventilation delivered by the assisted ventilation apparatus is greater than the ventilation delivered to the subject. Known devices which servo-control ventilation cope with this by collecting the exhaled air stream with a complex system of valves, and then measuring the exhaled ventilation. This is inappropriate for devices for use in a domestic setting during sleep, because of the attendant weight, complexity, and expense. The embodiment described compensates for the leak by continuously measuring the nonlinear conductance of the leak, and allowing for the instantaneous flow through the leak as a function of pressure.

Figure 5:
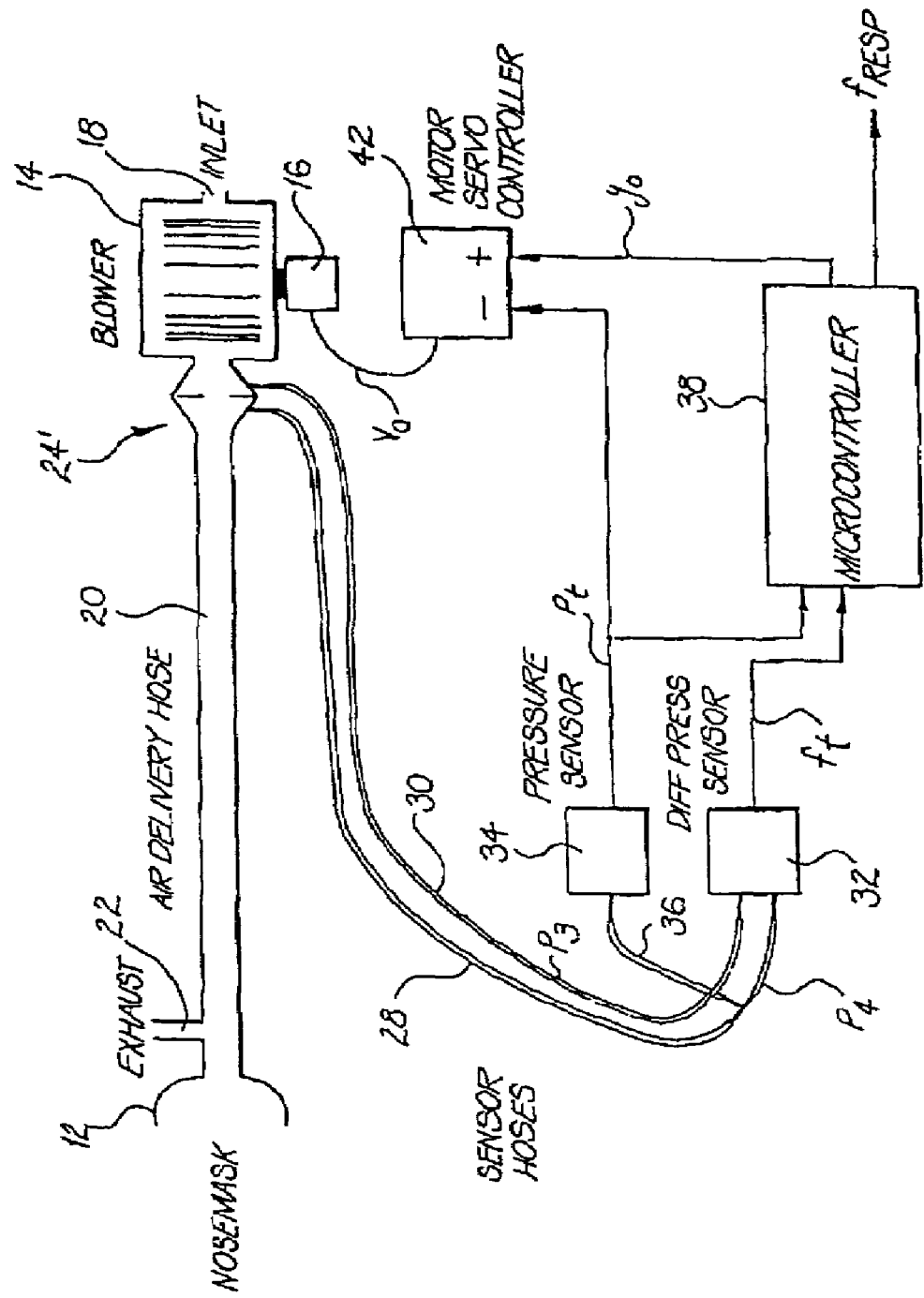
FIG. 5 shows a schematic diagram of ventilatory assistance apparatus of another embodiment.

FIG. 5 shows an alternate arrangement for ventilatory assistance apparatus 10' embodying the invention. In this arrangement, the pneumotachograph 24' is interposed between the turbine 14 and the delivery hose 20.

This arrangement removes the pressure sensing hoses and pneumotachograph from the region of the mask 12. The pressure at the mask, $P_{MASK}$, is calculated from the delivery pressure at the turbine 14, and from the pressure drop down the air delivery hose 20, which for any particular delivery hose is a known function of the flow at the pneumotachograph 24. Further, the microcontroller 38 must also calculate the flow through the mask from the flow at the turbine 14 less the flow through the exhaust 22, which for any particular exhaust is a known function of the pressure at the mask 12.

In more detail, this involves the steps of, firstly measuring the pressure $p_3$ at the turbine 14 with the pressure sensor 34 to produce an electrical signal $p_t$. Next the differential pressure $p_4-p_3$ is measured across the pneumotachograph 24' by the differential pressure sensor 32 to produce an electrical signal $f_t$. In a sampled manner, $p_t$ and $f_t$ are digitized to yield the sampled turbine pressure and flow signals $P_{TURBINE}$ and $F_{TURBINE}$.

The pressure at the mask $P_{MASK}$ and the sampled airflow at the mask $f_{MASK}$ 12 are calculated from the turbine pressure $P_{TURBINE}$ and the flow at the outlet of the turbine $F_{TURBINE}$ as follows:

1. Calculate the pressure drop $\Delta P_{TUBE}$ done the air delivery tube 20, from the flow at the outlet of the turbine $F_{TURBINE}$:

$\Delta P_{TUBE} = \text{sign}(F_{TURBINE}) \times K_1 (F_{TURBINE})^2 + K_2 F_{TURBINE}$ wherein $K_1$ and $K_2$ are empirically determined constants, and sign (X) is 1 for $X \leq 0$ and −1 otherwise.

2. Calculate the pressure at the mask, $P_{MASK}$, as the pressure at the turbine $P_{TURBINE}$ less the pressure deop $\Delta P_{TUBE}$ down the air delivery tube 20:

$P_{MASK} = P_{TURBINE} - \Delta P_{TUBE}$

3. Calculate the flow, $f_{EXHAUST}$, through the exhaust 22, from the pressure at the mask $P_{MASK}$:

$f_{EXHAUST} = \text{sign}(P_{MASK}) \times K_3 \sqrt{\text{abs}(P_{MASK})}$ where $K_3$ is determined empirically.

4. Calculate the flow, $f_{MASK}$, into the mask 12 as the flow at the turbine 14 less the flow through the exhaust 22:

$f_{MASK} = f_{TURBINE} - f_{EXHAUST}$

The foregoing embodiments describe low-pass filtering of both the instantaneous airflow and the square root of the instaneous pressure with a time constant t of 10 seconds. This time constant, t, can be advantageously dynamically adjustable.

If the conductance of the leak suddenly changes, then the calculated conductance will initially be incorrect, and will gradually approach the correct value at a rate which will be slow if the time constant of the low pass filters is long, and fast if the time constant is short. Conversely, if the impedance of the leak is steady, the longer the time constant the more accurate the calculation of the instaneous leak.

Therefore, it is desirable to lengthen the time constant if it is certain that the leak is steady, reduce the time constant if it is certain that the leak has suddenly changed, and to use intermediately longer or shorter time constants if it is intermediately certain that the leak is steady.

If there is a large and sudden increase in the conductance of the leak, then the calculated respiratory airflow will be incorrect. In particular daring apparent inspiration, the calculated respiratory airflow will be large positive for a time that is large compared with the expected duration of a normal inspiration. Conversely, if there is a sudden decrease in conductance of the leak, then during apparent expiration the calculated respiratory airflow will be large negative for a time that is large compared with the duration of normal expiration.

Therefore, an index of the degree of certainty that the leak has suddenly changed is derived, such that the longer the airflow has been away from zero, and by a larger amount, the larger the index; and the time constant for the low pass filters is adjusted to vary inversely with the index. In operation, if there is a sudden and large change in the leak, the index will be large, and the time constant for the calculation of the conductance of the leak will be small, allowing rapid convergence on the new value of the leakage conductance. Conversely, if the leak is steady for a long time, the index will be small, and the time constant for calculation of the leakage conductance will be large, enabling accurate calculation of the instantaneous respiratory airflow. In the spectrum of intermediate situations, where the calculated instantaneous respiratory airflow is larger and for longer periods, the index will be progressively larger, and the time constant for the calculation of the leak will progressively reduce. For example, at a moment in time where it is uncertain whether the leak is in fact constant, and the subject merely commenced a large sigh, or whether in fact there has been a sudden increase in the leak, the index will be of an intermediate value, and the time constant for calculation of the impedance of the leak will also be of an intermediate value. One advantage is that some corrective action will occur very early.

Another advantage is that there is never a moment where the leak correction algorithm is "out of control" and needs to be restarted, as described for prior art European Patent Publication No. 0 714 670 A2.

Figure 6:
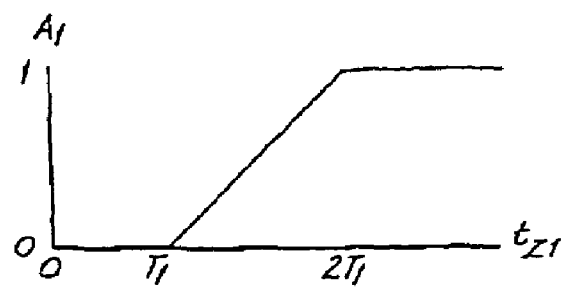
FIG. 6 shows a fuzzy membership function for the calculation of the extent $A_I$ to which the time $t_{ZI}$ since the most recent positive going zero crossing of the calculated respiratory airflow is longer than the expected time $T_I$.
Figure 7:
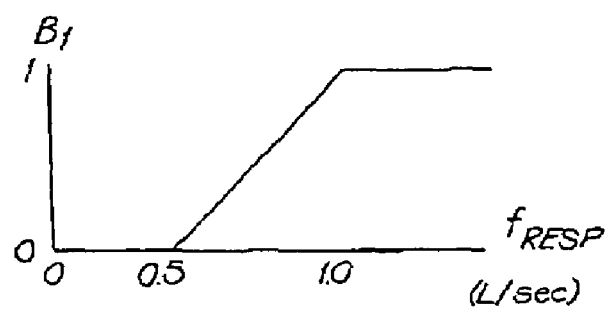
FIG. 7 shows a fuzzy membership function for the calculation of the extent $B_I$ to which the calculated inspiratory respiratory airflow $f_{RESP}$ is large positive.

In a preferred embodiment, the above index is derived using fuzzy logic. The fuzzy extent $A_1$ to which the airflow has been positive for longer than expected is calculated from the time $t_{ZI}$ since the last positive-going zero crossing or the calculated respiratory airflow signal, and the expected duration $T_I$ of a normal inspiration for the particular subject, using the fuzzy membership function shown in FIG. 6. The fuzzy extent $B_I$ to which the airflow is large and positive is calculated from the instantaneous respiratory airflow using the fuzzy membership function shown in FIG. 7. The instantaneous index $I_I$ of the degree of certainty that the leak has suddenly increased is calculated as the fuzzy intersection (lesser) of $A_1$ and $B_I$.

Figure 8:
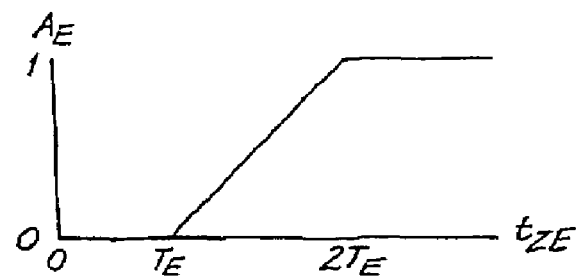
FIG. 8 shows a fuzzy membership function for the calculation of the extent $A_E$ to which the time $t_{ZE}$ since the most recent negative going zero crossing in the calculated respiratory airflow is longer than the expected time $T_E$.
Figure 9:
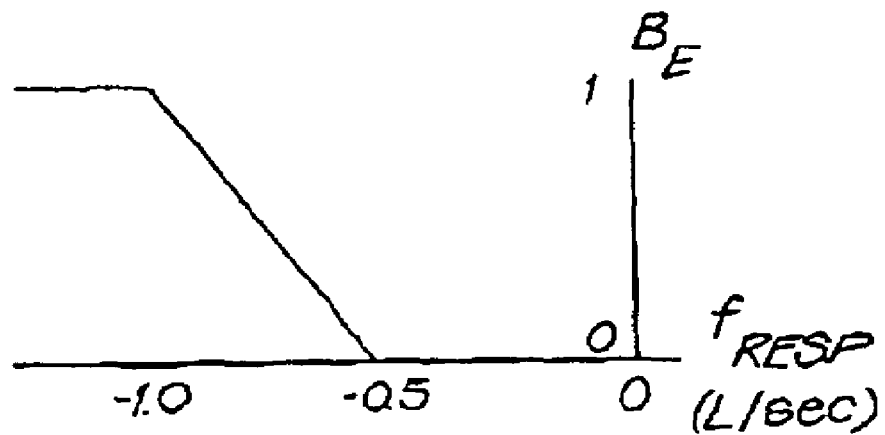
FIG. 9 shows a fuzzy membership function for the calculation of the extent $B_E$ to which the respiratory airflow $f_{RESP}$ is large negative.

Comparable calculations are performed for expiration as follows. The fuzzy extent $A_E$ to which the airflow has been negative for longer than expected is calculated from the time $t_{ZE}$ since the last negative-going zero crossing of the calculated respiratory airflow signal, and $T_E$, the expected duration of a typical expiration for the particular subject, using the membership function shown in FIG. 8. The fuzzy extent $B_E$ to which the airflow is large negative is calculated from the instantaneous respiratory airflow using the fuzzy membership function shown in FIG. 9. The instantaneous index $I_E$ of the degree of certainty that the leak has suddenly decreased is calculated as the fuzzy intersection of $A_E$ and $B_E$.

Figure 10:
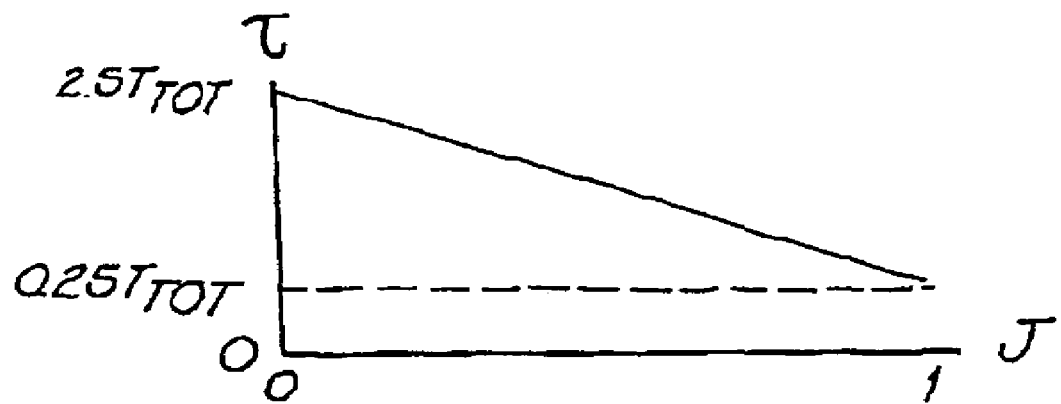
FIG. 10 shows the relation between an index J and time constant τ.

The instantaneous index I of the extent to which there has been a sudden change in the leak (either an increase or a decrease) is calculated as the fuzzy union (larger) of indices $I_I$ and $I_E$. The instantaneous index I is then passed through a peak detector followed by a low pass filter with a time constant of, for example 2 seconds, to yield the desired index J. Thus if index I becomes momentarily large, index J will be initially large and remain so for a few seconds. The time constant $\tau$ for the low pass filters used in the calculation of the conductance of the leak is then adjusted to vary inversely with the index J, as shown in FIG. 10. For example, if the expected duration of a normal respiratory cycle were 4 seconds the time constant is set to 10 seconds if the index J is zero, (corresponding to complete certainty that the leak is steady), and to 1 second if the index J is unity (corresponding to complete certainty that the leak is suddenly changing), and to intermediate values for intermediate cases.

The embodiments described refer to apparatus for the provision of ventilatory assistance, however, it is to be understood that the invention is applicable to all forms of mechanical ventilation and apparatus for the provision of continuous positive airway pressure treatment. The apparatus can be for the provision of a constant treatment pressure, multi-level (IPAP and EPAP) treatment or autosetting (adjusting) treatment or other forms of mechanical ventilation, including Proportional Assist Ventilation (PAV) as taught by M Younes in the above-noted text.

The methodology described can be implemented in the form of a computer program that is executed by the microcontroller described, or by discrete combinational logic elements, or by analog hardware.

The invention claimed is:

1. A method for determining an instantaneous leak flow from a patient mask during mechanical ventilation comprising the steps of:
    continuously determining instantaneous values of pressure in the mask and airflow through the mask;
    calculating conductance of a leak as a function of the values for pressure and airflow determined over a time interval that exceeds that of a normal breath; and
    calculating the instantaneous leak flow as a function of the calculated leak conductance and the determined instantaneous value of mask pressure.

2. The method for determining the instantaneous leak flow from a patient mask in accordance with claim 1 wherein said values are determined by taking direct measures of pressure and airflow.

3. The method for determining the instantaneous leak flow from a patient mask in accordance with claim 2 wherein the time interval over which pressure and airflow values are used to determine leak conductance varies in accordance with the rate at which the calculated leak conductance changes.

4. The method for determining the instantaneous leak flow from a patient mask in accordance with claim 1 wherein said mechanical ventilation is accomplished by forcing air to flow through an air delivery system, and said values are determined by taking direct measures of pressure and airflow in said air delivery system at a point remote from said leak, and calculating said values in accordance with the physical characteristics of the air delivery system and the direct measures.

5. The method for determining the instantaneous leak flow from a patient mask in accordance with claim 4 wherein the time interval over which pressure and airflow values are used to determine leak conductance varies in accordance with the rate at which the calculated leak conductance changes.

6. The method for determining the instantaneous leak flow from a patient mask in accordance with claim 1 wherein the time interval over which pressure and airflow values are used to determine leak conductance varies inversely with the rate at which the calculated leak conductance changes.

* * * * *